United States Patent [19]

Barradas

[11] Patent Number: 5,044,035
[45] Date of Patent: Sep. 3, 1991

[54] DENTAL CLEANING DEVICE

[76] Inventor: George Barradas, 15 Riverview Ct., Greenwich, Conn. 06831

[21] Appl. No.: 478,957

[22] Filed: Feb. 12, 1990

[51] Int. Cl.⁵ .............................................. A46B 13/00
[52] U.S. Cl. ...................................... 15/23; 15/21 R; 15/22.1; 15/22.2; 15/24
[58] Field of Search .................... 15/22.1, 22.2, 23, 24

[56] References Cited

U.S. PATENT DOCUMENTS

| | | | |
|---|---|---|---|
| 3,187,360 | 6/1965 | Spohr | 15/22.1 |
| 3,270,360 | 9/1966 | Kropp | 15/22.1 |
| 3,512,201 | 5/1970 | Taylor | 15/22.1 X |
| 3,661,018 | 5/1972 | Keefer et al. | 15/22.1 X |
| 3,984,890 | 10/1976 | Collis | 15/22.1 |
| 4,084,280 | 4/1978 | May | 15/22.1 |
| 4,113,376 | 9/1978 | Rodda | 15/256.52 X |
| 4,326,314 | 4/1982 | Moret et al. | 15/22.1 |
| 4,344,202 | 8/1982 | Hayat | 15/22.1 X |
| 4,397,055 | 8/1983 | Cuchiara | 15/22.1 |
| 4,603,448 | 8/1986 | Middleton et al. | 15/22.1 |
| 4,638,520 | 1/1987 | Eickmann | 15/22.1 |
| 4,698,869 | 10/1987 | Mierau et al. | 15/22.1 |
| 4,783,869 | 11/1988 | Lee | 15/22.1 |
| 4,827,550 | 5/1989 | Graham et al. | 15/22.1 |

FOREIGN PATENT DOCUMENTS 703419  2/1954  United Kingdom .................... 15/24

Primary Examiner—Paul T. Sewell
Assistant Examiner—BethAnne Cicconi
Attorney, Agent, or Firm—Alfred E. Miller

[57] ABSTRACT

An electrically-operated plaque-removing dental cleaning machine provided with an elongated rotating brush shaft having helical brush tufts strips thereon, and a partial shield spaced from the brush strips for collecting particles dislodged from the teeth when the brush strips engage and sweep the teeth and the inter-dental areas.

5 Claims, 3 Drawing Sheets

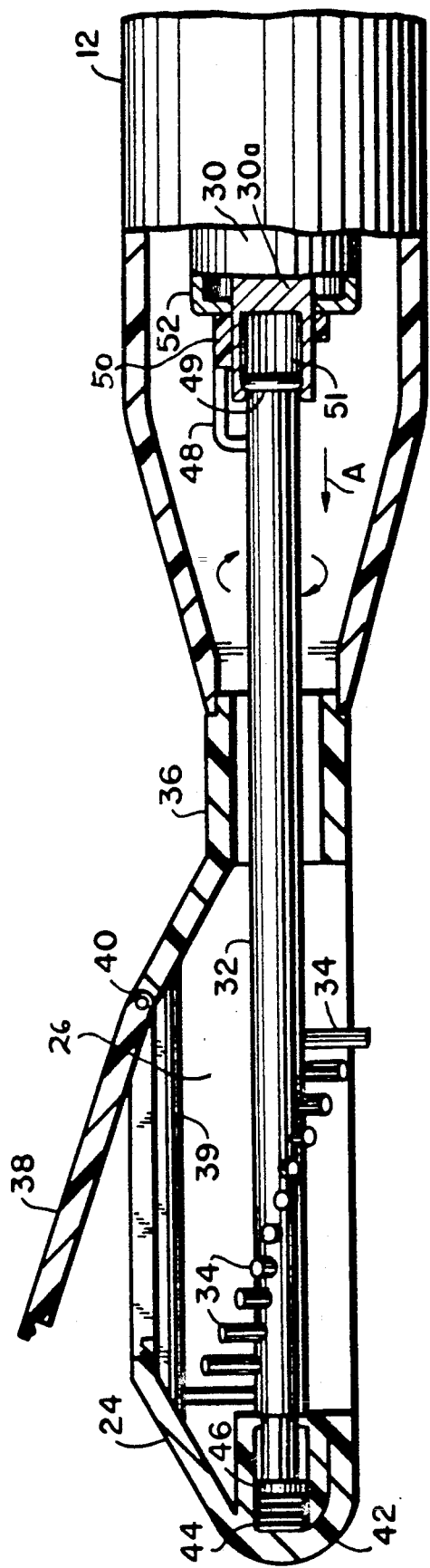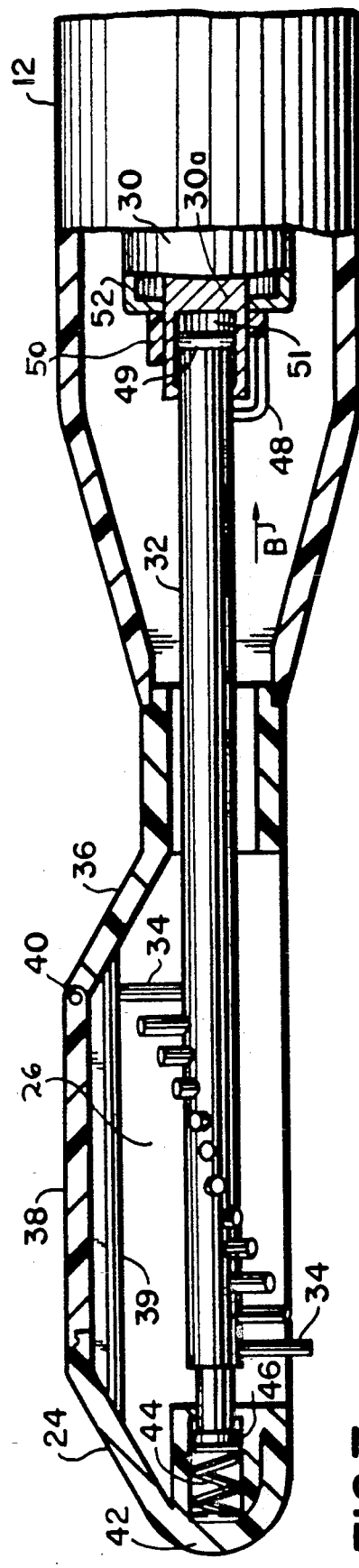

DENTAL CLEANING DEVICE

The present invention relates to a device for cleaning teeth as well as the interdental spaces in order to remove dental plaque, as well as to substantially reduce the formation of plaque on the teeth, thereby removing a large cause of incipient periodontal disease.

BACKGROUND OF THE INVENTION

Prior art devices and methods are know for brushing teeth in order to remove dental plaque. One such apparatus and method is shown in U.S. Pat. No. 4,156,620 to G. S. Clemens. This patent shows an apparatus having a plurality of tufts of filaments in which each of the tufts is rotated about its own axis and where each of the tufts counter-rotates with respect to the adjacent tufts. However, it is believed that the structure and operation of the device in the above mentioned patent is complex and costly. The present invention is a simplified and effective means for tooth cleaning with a device for removing plaque and which also prevents the formation of plaque on the teeth, and is reliably effective for the purposes intended.

SUMMARY OF THE INVENTION

It is an object of the present invention to provide a dental cleaning device a having hand-held rotatable brush which is helically arranged on an elongated shaft and which is provided with a shield mounted adjacent to the helical brush. The shield has a collection groove at the center thereof for accumulating plaque and other debris removed from the surface of the teeth being brushed and cleaned. Thus, the rotating helical brush sweeps particles that have been dislodged from the teeth to the center of the shield for removal.

It is a further object of the present invention to rotate the helical brush in one direction and then counter rotate the brush in the opposite direction in a continual operation.

It is another object of the present invention to construct a helical brush and a shield in which the dislodged particles from the surface of the teeth are conducted to the end of the shield for easy removal therefrom.

It is still another object of the present invention to utilize a spiral-shaped brush in which the tuft lengths on the brush device are of various heights in order to effectively sweep the particles and plaque removed from the teeth into the receiver for the debris.

It is a further object of the present invention to provide a polishing attachment for the rotatable shaft of the helical brush so that the teeth can be treated alternately with the attachment for cosmetic appearance.

BRIEF DESCRIPTION OF THE DRAWINGS

In order that the invention may be more clearly understood it will now be disclosed in further detail with reference to the accompanying drawing wherein:

FIG. 6 is a sectional view, partly in elevation, of an alternate embodiment of the invention in which the drive shaft in one position has both rotational and translation movement, and FIG. 7 is a view similar to FIG. 6 with the drive shaft is another position.

DESCRIPTION OF THE PREFERRED EMBODIMENTS

Figure 1:
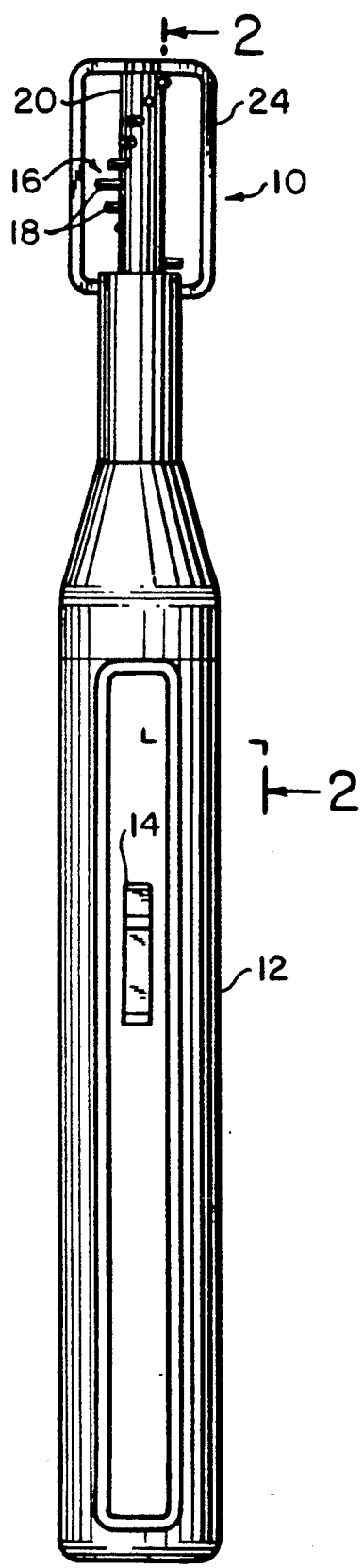
FIG. 1 is a front elevational view of the cleaning device for teeth constructed in accordance with the teachings of the present invention.
Figure 2:
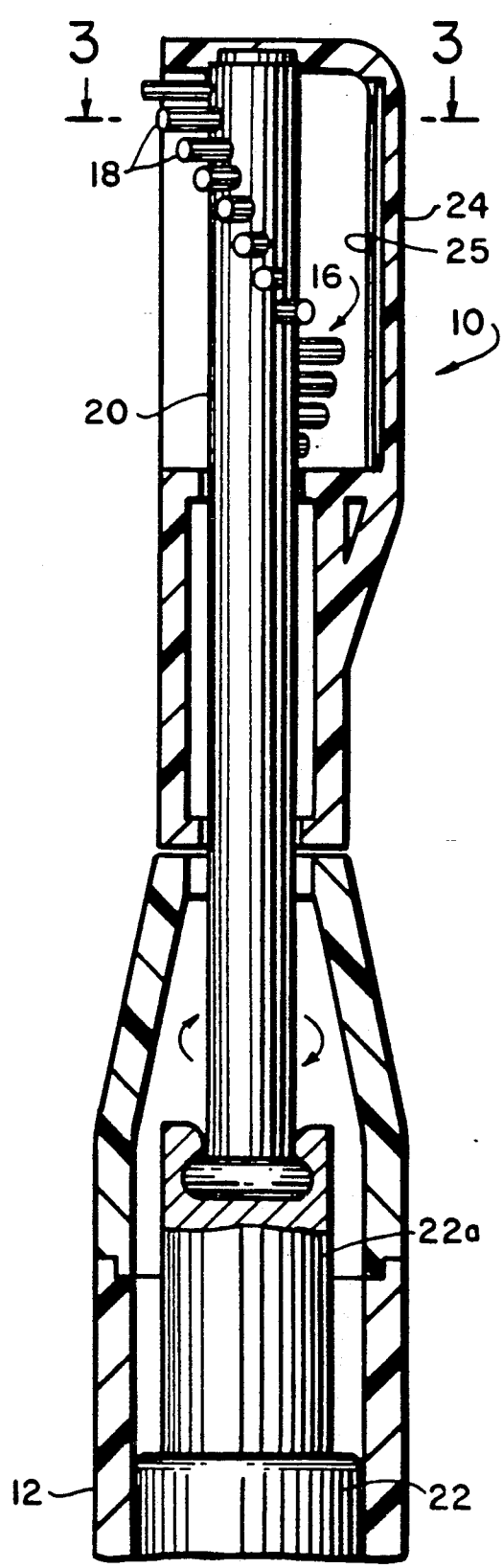
FIG. 2 is an enlarged side elevation, partially in section, showing the device in FIG. 1.
Figure 3:
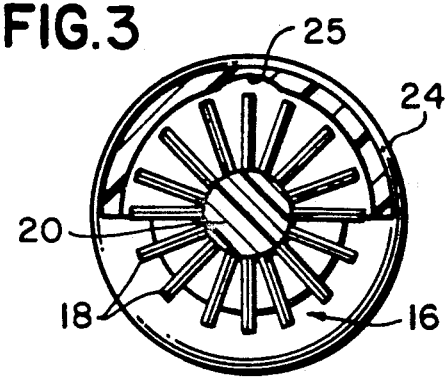
FIG. 3 is a view taken along the lines 3—3 of FIG. 2.

A device for cleaning teeth in order to remove dental plaque is shown in FIGS. 1-4 having an elongated head member, referred to generally by the reference numeral 10, and a base or handle portion 12 provided with a switch 14. A brush member referred to generally by the numeral 16 is provided with a series of tufts 18 each preferable composed by a multiplicity of filaments disposed helically or spirally along the brush shaft 20. The shaft 20 is driven by an electric motor 22 having a motor shaft 22a, which is of the reversible type, and which causes the helical brush to rotate in a single, or in opposite directions. The elongated helical brush 16 is partially covered by a shield 24 which serves two functions; that is, to prevent the user's lips and gums from being lacerated by the rotating brush, and also to collect the debris and particles pushed away from the tooth surfaces and the inter-dental areas as the rotating brush sweeps the teeth. Thus, the brush picks up particles that are dislodged from the teeth and moves those particles into the space 26 between the rotating brush bristles 18 and the shield 24 and can be collected in the pocket 25 in the shield. In the alternative, the tufts 18 on the brush shaft may be arranged in a manner to cause the dislodged particles from the teeth and inter-dental areas to be swept toward the end of the brush, as the shaft rotates.

Figure 4A:
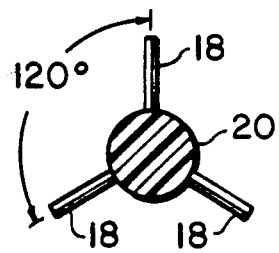
FIG. 4a is a front elevational view of a brush shaft having three helical rows.
Figure 4:
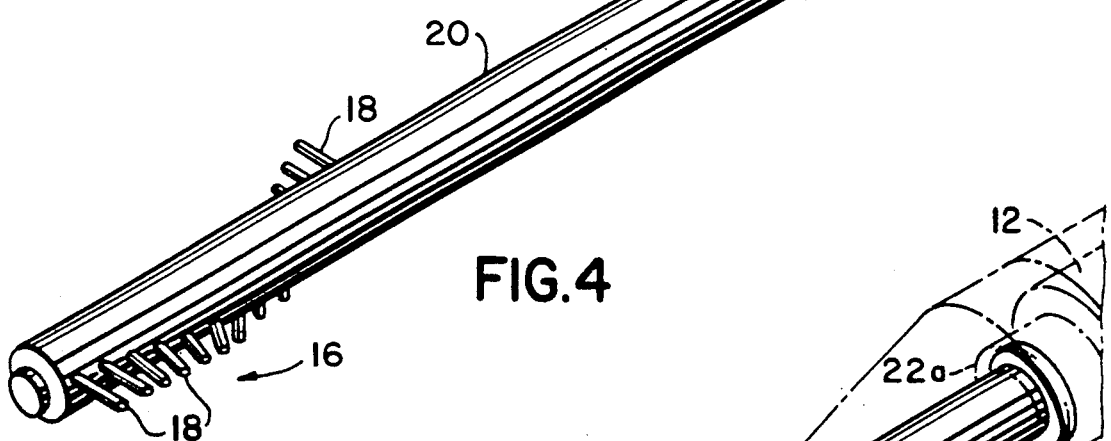
FIG. 4 is a view taken along the lines 4—4 of FIG. 1.
Figure 5:
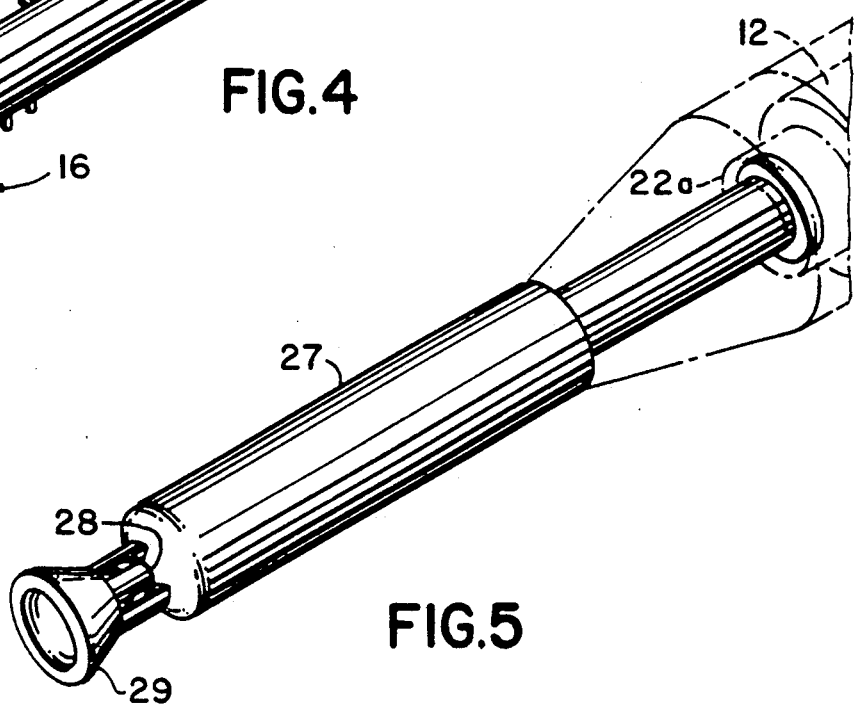
FIG. 5 is a perspective view of an attachment to the cleaning device of FIG. 1 for polishing the teeth.

It should be evident that the present device, because it has a rotating shaft with helically or spirally arranged tufts over a considerable length, will be able to contact and sweep a multiplicity of teeth at any given time, and at the same time protect the lips and gums from being lacerated by the rotating brush. A preferred form of arrangement of the tufts or bristles on the rotating shaft 18 is shown in FIGS. 4 and 4a where the individual tufts elements are mounted in a spiral manner. In FIG. 4a, the preferred embodiment is shown wherein the helical brush strips are placed about 120° apart.

When it becomes desirable to clean the particles and debris lodged in the space 26 between the rotating brush and the shield 24 it is only necessary to place the brush head under a faucet and permit running water to flush the particles and debris away.

An additional feature of the present invention is shown in FIG. 4 in which a polishing device 27 is seen having a rubber cup 29, which can be removably attached to an end post 28 of the rotatable motor shaft 22a after the cover or shield 24, as well as the brush member 16, have been removed.

Referring now to FIG. 6 and 7, an alternate embodiment of the present invention is shown having a motor 30, a motor shaft 30a and a rotating brush shaft 32 operated by said motor with helical bristles 34 on said shaft for cleaning the teeth, together with a shield 36 having a openable section 38 which is pivoted to the point 40 on the shield 36. The shield is also provided with a housing 42 having a spring 44 therein engaging the end 46 of the shaft 42.

Mounted on the rotating brush shaft 32 is a cam finger 48 which is adapted to be biased into engagement with ramp-like a cam 50 on the motor housing 52. Thus, when the motor rotates the motor shaft 30a the cam finger 48 engages the cam 50, since the spring 46 biases the shaft 32 inwardly, as seen in FIG. 7, which ensures that the cam finger 48 continually engages the cam 50. The brush shaft 32 is provided with a pin 49 which is slidable in slot 51 of the motor shaft 30a, as seen in FIGS. 6 and 7, thereby permitting rectilinear or translating movement of the brush shaft 32, as illustrated by the arrows A and B in FIGS. 6 and 7 respectively. Thus, as the brush shaft 32 rotates, the cam finger 48 rides over the ramp-like cam 50 thus causing the shaft 32 to reciprocate to permit limited linear or translating movement of the shaft 32. Consequently, the shaft 32 will not only rotate in a single or reverse directions, but also moves linearly back and forth, thereby eliminating the necessity for manual back and forth movement of the dental cleaning device on the teeth. It should be evident that use of the present device will effectively dislodge particles from the teeth and to assist in the removal of plaque on the surfaces, crevices, as well as the inter-dental areas of the teeth. In addition, as seen in FIG. 7, an internal rib 39 is shown on the underside of the section 38 of the shield 24 which functions as a wiper to remove particles that cling to the tufts as the brush shaft rotates and impacts the rib.

While the present invention has been disclosed and described with reference to certain embodiments thereof it is apparent that other variations and modifications may be made which fall within the true spirit and scope of the inventions, as defined in the following claims:

What I claim is:

1. A dental cleaning device for cleaning the teeth and inter-dental spaces comprising a handle, a motor mounted in said handle being provided with a shaft and a housing, a brush shaft operatively connected to said motor shaft for rotation, a plurality of brush tuft strips helically arranged on said brush shaft, a partial shield attached to said dental cleaning device for said brush tuft strips mounted adjacent thereto but spaced therefrom for collecting particles that are dislodged from said teeth when said rotating helical brush tuft strips contacts said teeth, means on said motor housing and brush shaft for causing a rectilinear movement of said brush shaft while said shaft rotates, said means being a ramp-like cam on the motor housing, a cam finger mounted on said brush shaft, a pin on said brush shaft, a slot in said motor shaft, said pin being mounted in said slot and adapted for rectilinear movement in said slot when said cam finger engages said ramp-like cam during rotation of said brush shaft, and a compression spring to urge the cam finger into engagement with said ramp-like cam and thereby imparting both rotational and reciprocating movement to said brush shaft.

2. A dental cleaning device as claimed in claim 1 wherein said shield is provided with a pivotable door opening in the top thereof for cleaning purposes.

3. A dental cleaning device as claimed in claim 1 further comprising an internal rib on the underside of said shield adjacent to said brush tuft strips whereby said rib functions as a wiper to remove particles that cling to the tufts as the brush shaft rotates and said brush tuft strips impace said rib.

4. A dental cleaning device as claimed in claim 1 further comprising a housing at one end of said shield including said compression spring in which one end thereof engages an interior surface of said housing and the other end thereof engages the free end of said brush shaft.

5. A dental cleaning device as claimed in claim 1 further comprising a dental polishing attachment provided with a shaft, and means for removably fixing said dental polishing shaft to said motor after said brush shaft and shield have been removed.

* * * * *